(12) United States Patent
Jackson et al.

(10) Patent No.: US 9,689,023 B2
(45) Date of Patent: *Jun. 27, 2017

(54) METHODS FOR MOLECULAR DETECTION

(75) Inventors: George Jackson, Pearland, TX (US); Christopher Quan, Houston, TX (US)

(73) Assignee: BioTex, Inc., Houston, TX (US)

( * ) Notice: Subject to any disclaimer, the term of this patent is extended or adjusted under 35 U.S.C. 154(b) by 700 days.

This patent is subject to a terminal disclaimer.

(21) Appl. No.: 13/244,638

(22) Filed: Sep. 25, 2011

(65) Prior Publication Data

US 2012/0015359 A1 Jan. 19, 2012

Related U.S. Application Data

(63) Continuation of application No. PCT/US2010/020285, filed on Jan. 6, 2010, which is a continuation of application No. 12/479,806, filed on Jun. 6, 2009, now Pat. No. 8,034,569, application No. 13/244,638, which is a continuation-in-part of application No. 13/212,136, filed on Aug. 17, 2011, now abandoned, which is a continuation of application No. 12/479,806, filed on Jun. 6, 2009, now Pat. No. 8,034,569.

(60) Provisional application No. 61/059,435, filed on Jun. 6, 2008.

(51) Int. Cl.
*C12Q 1/68* (2006.01)
*G01N 33/53* (2006.01)

(52) U.S. Cl.
CPC ......... *C12Q 1/6804* (2013.01); *C12Q 1/6844* (2013.01); *G01N 33/5308* (2013.01); *C12Q 2525/205* (2013.01); *C12Q 2537/161* (2013.01)

(58) Field of Classification Search
None
See application file for complete search history.

(56) References Cited

U.S. PATENT DOCUMENTS 6,562,575 B1 * 5/2003 Dahl ................................. 435/5
8,034,569 B2 * 10/2011 Jackson et al. ............. 435/6.12
2002/0192658 A1 * 12/2002 Ward et al. ....................... 435/6

FOREIGN PATENT DOCUMENTS

SE WO 2007107743 A1 * 9/2007 ............. C12Q 1/682

OTHER PUBLICATIONS

Yang, L., et al. Real-time rolling circle amplification for protein detection. Analytical Chemistry, vol. 79(9), p. 3320-3329, 2007.*

* cited by examiner

*Primary Examiner* — Prabha Chunduru
*Assistant Examiner* — Suryaprabha Chunduru
(74) *Attorney, Agent, or Firm* — Christopher Quan

(57) ABSTRACT

This invention relates to methods for molecular detection, particularly to methods utilizing target-specific molecular probes. In exemplary embodiments, target-specific molecular probes include single-stranded deoxyribonucleic acid (DNA) or ribonucleic acid (RNA) aptamers. In general, the molecular probe may bind with relatively high specificity to a given target. In one aspect, a method for molecular detection comprises a molecular probe paired to a reporter molecule wherein the molecular probe impairs the amplification of the reporter molecule in the absence of the target molecule.

18 Claims, 5 Drawing Sheets

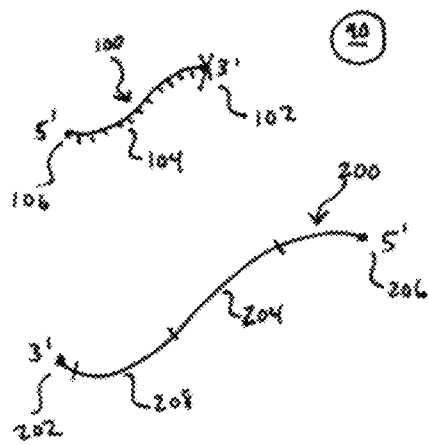
FIG. 1
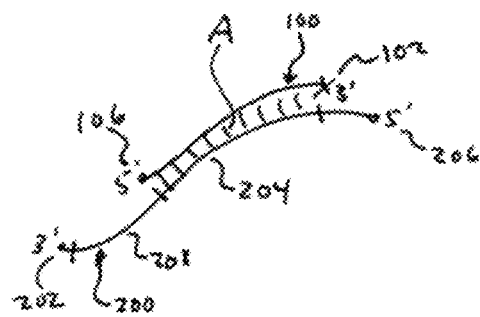
FIG. 1a
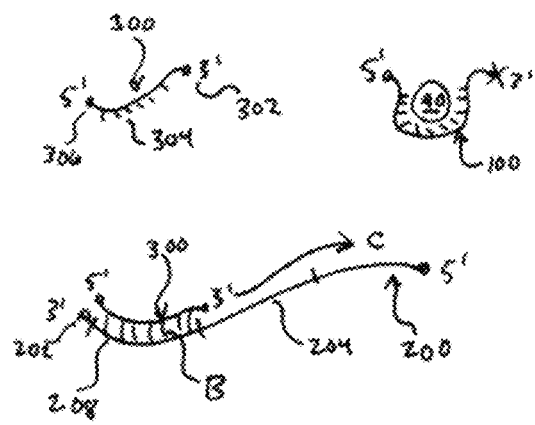
FIG. 1b
FIG. 1c
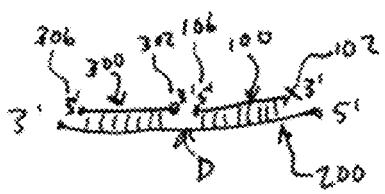
FIG. 1d
FIG. 1e

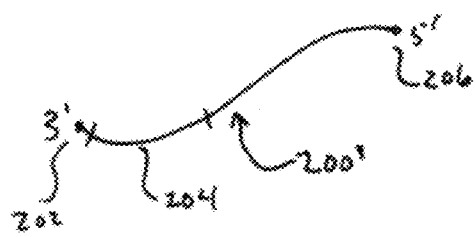
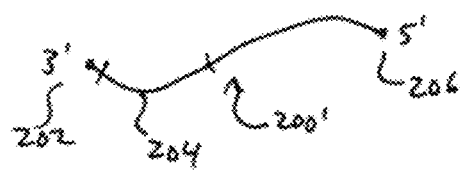
FIG. 2a
FIG. 2
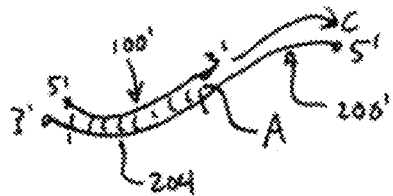
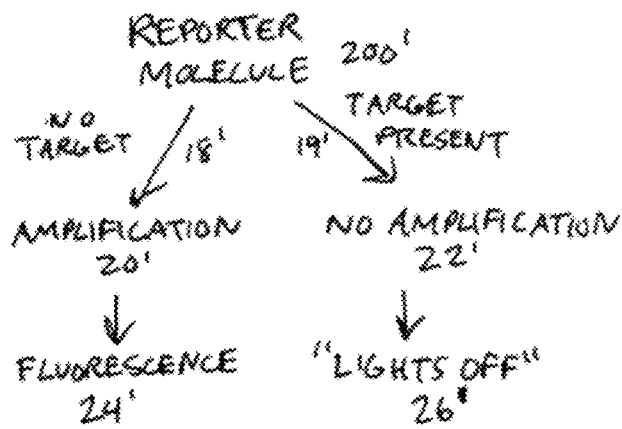
FIG. 2b
FIG. 2c

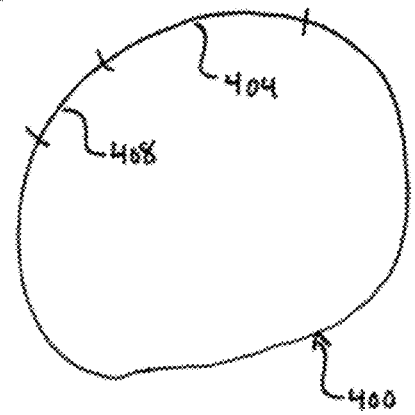
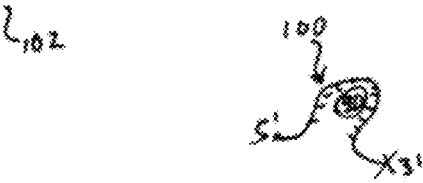
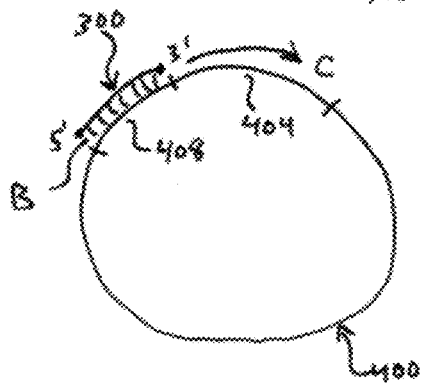
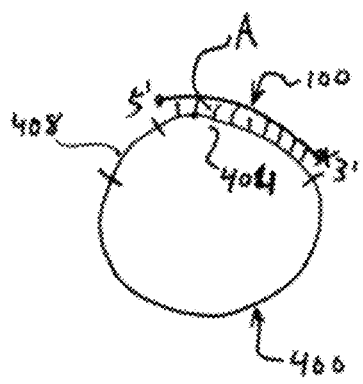
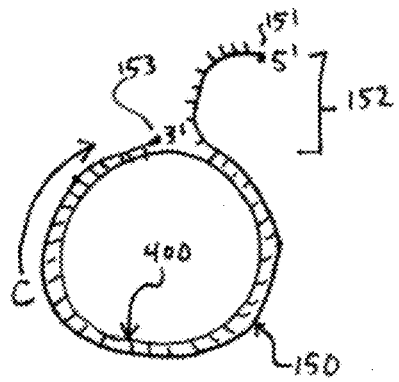
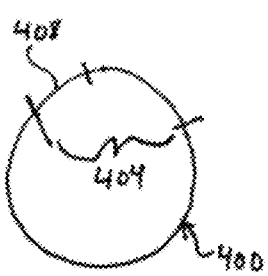
FIG. 3
FIG. 3a
FIG. 3b
FIG. 3c
FIG. 4
FIG. 5

METHODS FOR MOLECULAR DETECTION

CROSS-REFERENCE TO RELATED APPLICATIONS

This application is a continuation of and claims the priority of PCT International Patent Application Ser. No. PCT/US10/20285, which is pending, filed Jan. 6, 2010, entitled "METHODS FOR MOLECULAR DETECTION", which claims the priority of U.S. patent application Ser. No. 12/479,806, filed Jun. 6, 2009, entitled "METHODS FOR MOLECULAR DETECTION", the entire contents of all of which are hereby incorporated by reference.

This application is a continuation-in-part of and claims the priority of U.S. patent application Ser. No. 13/212,136, which is pending, filed Aug. 17, 2011, entitled "METHODS FOR MOLECULAR DETECTION", which is a continuation of U.S. patent application Ser. No. 12/479,806, filed Jun. 6, 2009, entitled "METHODS FOR MOLECULAR DETECTION", which claims the priority of U.S. provisional patent application Ser. No. 61/059,435, filed Jun. 6, 2008, entitled "METHODS FOR MOLECULAR DETECTION", the entire contents of all of which are hereby incorporated by reference.

SEQUENCE LISTING

The deoxyribonucleic acid sequences 5'-CCGTCTTCCAGACAAGAGTGCAGGG-3' and 5'-ATGCCCCTGCACTCTTGTCTGGAAGACGG-3', titled SEQ ID NO 1 and SEQ ID NO 2, respectively, are hereby incorporated by reference to the ASCII text file entitled "PSEQ1_P1019US02.txt", created Aug. 17, 2011, of 867 bytes in size.

FIELD OF THE INVENTION

This invention relates to methods for molecular detection, for example, to methods utilizing target-specific molecular probes.

BACKGROUND OF THE INVENTION

Proteomics is often considered the next step in the study of biological systems, after genomics. The challenge of unraveling the proteome is generally considered much more complicated than genomics, primarily because the proteome differs from cell to cell and constantly changes through biochemical interactions with the genome and the environment. An organism has radically different protein expression in different parts of its body, different stages of its life cycle and different environmental conditions. Another major difficulty is the complexity of proteins relative to nucleic acids; in humans there are about 25,000 identified genes but an estimated ~500,000 proteins derived from these genes. This increased complexity derives from mechanisms such as alternative splicing, protein modification (glycosylation, phosphorylation) and protein degradation. The level of transcription of a gene gives only a rough estimate of its level of expression into a protein. An mRNA produced in abundance may be degraded rapidly or translated inefficiently, resulting in a small amount of protein. Additionally, many proteins experience post-translational modifications that profoundly affect their activities; for example some proteins are not active until they become phosphorylated. Methods such as phosphoproteomics and glycoproteomics are used to study post-translational modifications. Many transcripts also give rise to more than one protein through alternative splicing or alternative post-translational modifications. Finally, many proteins form complexes with other proteins or RNA molecules, and only function in the presence of these other molecule.

Over the years, antibody-mediated detection has proven to be one of the most robust and sensitive assays for any non-nucleic-acid target. Small-molecule toxins and other bioactive compounds, important protein "biomarkers" indicating disease and/or pathogen activity, and even whole viral capsids can be readily detected and quantified by immunoassays. Despite incredible successes, antibody-based diagnostics suffer several well-recognized drawbacks.

SUMMARY OF THE INVENTION

This invention relates to methods for molecular detection, for example, to methods for molecular detection utilizing target-specific molecular probes. In general, the target-specific molecular probes, in conjunction with reporter molecules, may be used to detect the presence or absence of a specific target. The target-specific molecular probes may bind to target molecules, if present, such as for example, in competition and/or with higher affinity than to a reporter molecule. In one embodiment, the methods regulate detection of reporter molecules.

In general, a target molecule may refer to any appropriate targets, which may include, but are not limited to atomic/ionic targets, molecular targets, biomolecules, proteins, molecular complexes, cells, tissues, viruses, and/or any other appropriate target or combinations thereof.

A reporter molecule may generally be a molecule that may be substantially detectable and/or experience a substantial change in detectability under certain conditions of an assay. The detectability of the reporter molecule may be, for example, accomplished by regulating amplification of the reporter molecule in an amplification reaction.

In exemplary embodiments, target-specific molecular probes include substantially single-stranded nucleic acids and/or modifications thereof. In general, a molecular probe may bind with relatively high specificity to a given target and an example may be or include an aptamer. Aptamers may generally include, but are not limited to, single-stranded nucleic acid, such as, for example, single-stranded DNA (ssDNA), single-stranded RNA (ssRNA), and/or a combination thereof; at least a portion of double-stranded nucleic acid, such as, for example, double-stranded DNA (dsDNA), double-stranded RNA (dsDNA), and/or combinations thereof; modified nucleotides and/or other useful molecules, moieties, and/or other functional chemical components, or combinations thereof; or combinations thereof or similar.

In an exemplary embodiment of the invention, a reporter molecule may bind and/or hybridize with a molecular probe in competition with a target molecule of the molecular probe in the presence of a target molecule in the sample, for example. In some embodiments, the molecular probe may bind with substantially similar affinity to the reporter molecule and the target molecule. In other embodiments, the molecular probe may bind to the target molecule with higher affinity than to the reporter molecule, such as, for example, in a substantially irreversible manner.

In one aspect, a method for molecular detection includes utilizing a molecular probe paired to a reporter molecule such that the molecular probe impairs the detection and/or amplification of the reporter molecule in the substantial absence of the target molecule of the molecular probe. In general, amplification of a reporter molecule, such as, for example, a nucleic acid reporter molecule, may refer to generating substantial copies of a reporter molecule, complements of a reporter molecule, sections of a reporter molecule or complements thereof, both the reporter molecule and complements thereof, and/or concatenations and/or other modifications or combinations thereof. For example, the molecular probe may bind to a conjugate region of the reporter molecule, such as, more for example, a nucleic acid region having a complementary sequence.

In an exemplary embodiment, the molecular probe with some specific binding affinity to a target molecule is a substantially single-stranded nucleic acid or aptamer which is at least partially complementary in sequence to a reporter molecule, which may be a substantially single-stranded nucleic acid. The molecular probe may further be substantially non-extendable by nucleic acid polymerases, such as by, for example, inclusion of a non-extendable 3' end, such as a sequence span that is not complementary to the reporter molecule, a chemically non-extendable moiety, a sterically blocking moiety, and/or a modified base, such as a dideoxy-base lacking a 3' —OH group to form a phosphodiester bond. Without the presence of a target molecule in a sample, the molecular probe may thus be free to hybridize with the complementary sequence of the reporter molecule. The non-extendable molecular probe may then inhibit amplification by polymerase action. This may also be desirable as the molecular probe may also not be amplified or extended by polymerases, which may thus substantially preserve the amount and structure of the molecular probe in the system.

In general, modifications, such as those discussed above, may also be present on the 5' end of the molecular probe such that it may block and/or interfere with any exonuclease and/or strand displacement by enzymes.

In general, a primer may be a short single-stranded nucleic acid which may be at least partially complementary to a template nucleic acid, such as a reporter molecule, such that hybridization of the primer to the template may be utilized as a starting point for a polymerase to amplify the template. In general, any appropriate quantitative or semi-quantitative nucleic acid amplification reaction may be utilized for amplification and detection. Such reactions may include, for example, various embodiments of polymerase chain reaction (PCR), more for example, quantitative PCR (QPCR). The amplification reaction may produce multiple copies of, for example, the reporter molecule, etc. . . . , in some relation to the amount of molecular probes bound to target molecules. The amplification may produce an increased amount of nucleic acids which may be detectable, such as, for example, by nucleic acid recognizing fluorescent dyes. Thus, such quantitative or semi-quantitative nucleic acid amplification reactions may generally include a reporter for determining the amount of, for example, nucleic acid present in a sample. The detection of the amplified reporter molecules may then be utilized to correlate the amount of target molecule present in a sample.

In embodiments where the presence of the target sequesters the non-extendable molecular probe, which may also hybridize to and block amplification of the reporter molecule, the result may be amplification of the reporter molecule and may generally be referred to as a "lights-on" assay as the "lights on" of the fluorescent dye may generally indicate the substantial presence of target molecule.

In some embodiments, a sample which may contain target molecules may be first contacted with a substantially known amount of molecular probe. In general, it may be desirable for the molecular probe to bind to the target molecules in a known proportion, such as, for example, one probe to one target molecule. The reporter molecule may then be added in a substantially known amount such that any remaining unbound molecular probes may hybridize to the reporter molecules. At least one primer may then be added to hybridize to the reporter molecules and an amplification reaction may then be utilized to amplify the reporter molecules not hybridized to a molecular probe.

In other embodiments, when the reporter molecules are present in a similar amount to the amount of the molecular probe, at least a portion of the amount of reporter molecules may be unhybridized to a molecular probe when a small amount of target molecules is present. At least one primer may then be utilized to hybridize to those reporter molecules not hybridized to the probe so that these remaining reporter molecules may then be amplified.

In some exemplary embodiments, the reporter molecule may include a circular single-stranded nucleic acid. The reporter molecule may in general hybridize to a molecular probe, for example, a non-extendable molecular probe, in the absence of a target molecule, as discussed above. The non-extendable molecular probe, for example, may then inhibit amplification of the reporter molecule, as also discussed above. In the presence of a target molecule, however, the molecular probe may be bound to the target molecule and then at least one primer may be utilized to amplify the reporter molecule which are not hybridized to the probe in this instance. In general, it may be desirable, for example, to utilize rolling circle amplification or a similar amplification reaction on a circular reporter molecule. In rolling circle amplification, for example, a polymerase may extend the primer hybridized to the circular template, as in standard PCR. The polymerase may then continue extension around the circular template for the duration of the amplification as the circular template may not include any defined end or point of termination of extension. This may be desirable as a relatively large amount of amplification product may be generated without the typical melting and annealing steps of standard PCR. The amplification product may generally be a linear single-stranded nucleic acid which may be a concatenation of the complementary sequence of the circular template.

In other embodiments, the molecular probe may be an extendable single-stranded nucleic acid and may substantially act as a primer for the reporter molecule. Thus, in the absence of target molecule, the molecular probe may hybridize to the reporter molecule and act as a primer which may be extended in an amplification reaction, as discussed above. In the presence of target molecule, the molecular probe may be bound to the target molecule and thus it may not act as a primer for the reporter molecule, which may result in substantially no amplification of the reporter molecule. Thus, the detection of amplification product may generally correlate to the absence of target molecule in a sample while the detection of no or substantially no amplification product (or very little) may generally correlate to the presence of target molecule. This form of assay may generally be referred to as "lights-off" as a fluorescent reporter would be "lights off" in the substantial presence of target molecule. This may be utilized with both circular and linear reporter molecules.

In general, rolling circle amplification may utilize nucleic acid polymerases that may include strand displacement activity. Strand displacement activity may be useful in displacing the amplified product from the template as the polymerase circles around and meets the starting end (e.g. the 5' end of original primer). Without the displacement activity, the amplification may not substantially continue as the hybridized strand may block the polymerase from continuing to read the circular template.

In an exemplary embodiment, the primer for a "lights-on" rolling circle amplification may share at least a portion of its sequence with the molecular probe. For example, the complementary regions on the reporter molecule for the primer and the molecular probe may substantially overlap or the primer region may also be part of the molecular probe region.

In another embodiment, the primer for a "lights-on" rolling circle amplification may bind directly adjacent to the binding site of the molecular probe on the reporter molecule. For example, there may be no sequence gap between the primer and the molecular probe when both are hybridized to the reporter molecule. The molecular probe and the primer may then be attached and/or connected, such as, for example, by a ligation reaction, such that the molecular probe and the primer may become joined as a single nucleic acid strand. This may be desirable as the ligation may present no strand breakage or "knick" for a polymerase enzyme to recognize, as a knick may serve as a starting point for polymerase action and polymerases with sufficient strand-displacement activity may displace some of the hybridized molecular probe.

In an exemplary embodiment of the invention, the method for molecular detection includes:
  contacting a molecular probe and a reporter molecule with a sample that may or may not contain a target; and
  performing a quantitative or semi-quantitative amplification reaction on the reporter molecule;
wherein the molecular probe binds to a conjugate region of the reporter molecule in the absence of the target molecule and impairs amplification of the reporter molecule.

Optionally, the amplification reaction may further include at least one primer which is substantially complementary to at least a portion of said reporter molecule.

In one aspect, the molecular probes have competitive binding affinity for the target and the reporter molecule. In another aspect, the molecular probes may have higher binding affinity for the target than for the reporter molecules.

In another exemplary embodiment of the invention, the method for molecular detection includes:
  contacting a molecular probe and reporter molecule with a sample that may or may not contain a target; and
  performing a quantitative or semi-quantitative amplification reaction on the reporter molecule;
wherein the molecular probe binds to a conjugate region of the reporter molecule in the absence of the target and enables amplification of the reporter molecule.

In one aspect, the molecular probes may have competitive binding affinity for the target and the reporter molecule. In another aspect, the molecular probes have higher binding affinity for the target than for the reporter molecule. In a further aspect, the molecular probes may be substantially complementary to at least a portion of the reporter molecule.

In yet another exemplary embodiment of the invention, the method for molecular detection includes:
  contacting at least one molecular probe with a sample that may or may not contain a target;
  contacting at least one reporter molecule with the at least one molecular probe and the sample; and
  performing a quantitative or semi-quantitative amplification reaction on the reporter molecules;
wherein the at least one molecular probe binds to at least one conjugate region of the at least one reporter molecule in the absence of the target and inhibits amplification of the at least one reporter molecule.

In one aspect, the at least one molecular probe has competitive binding affinity for the target and the at least one reporter molecule. In another aspect, the at least one molecular probe has higher binding affinity for the target than for the at least one reporter molecule. In a further aspect, the method may also include partitioning the at least one molecular probe bound to the target prior to contacting the at least one molecular probe with the at least one reporter molecule.

In a further exemplary embodiment of the invention, the method for detecting includes, for example:
  obtaining at least one aptamer molecular probe for at least one target molecule and at least one nucleic acid strand having at least one conjugate region for the aptamer; and
  contacting the at least one aptamer and nucleic acid strand with a sample which may contain at least one target molecule for performing a quantitative or semi-quantitative nucleic acid amplification reaction on the nucleic acid strand;
wherein the at least one aptamer binds to the at least one conjugate region of the nucleic acid strand in the absence of the target molecule and interrupts nucleic acid amplification thereof.

In one aspect, the method may also include providing at least one primer for the nucleic acid strand.

In yet a further exemplary embodiment of the invention, the method includes, for example:
providing at least one aptamer molecular probe for at least one target molecule and at least one nucleic acid strand which includes at least one conjugate region for the at least one aptamer; and
contacting the at least one aptamer and nucleic acid strand with a sample which may contain target molecule for performing a quantitative or semi-quantitative nucleic acid amplification reaction on the nucleic acid strand;
wherein the at least one aptamer binds to the at least one conjugate region of the nucleic acid strand in the absence of target molecule and interrupts nucleic acid amplification thereof.

In one aspect, the method may also include providing at least one primer for the nucleic acid strand.

In still a further exemplary embodiment of the invention, the method includes, for example:
selecting at least one aptamer molecular probe for at least one target molecule and at least one nucleic acid strand which includes at least one conjugate region for the at least one aptamer; and
contacting the at least one aptamer and nucleic acid strand with a sample which may contain at least one target molecule for performing a quantitative or semi-quantitative nucleic acid amplification reaction on the nucleic acid strand;
wherein the at least one aptamer binds to the at least one conjugate region of the nucleic acid strand in the absence of target molecule and interrupts nucleic acid amplification thereof.

In one aspect, the method may also include providing at least one primer for the nucleic acid strand.

The present invention also relates to molecular detection of multiple targets. In one embodiment, multiple probes may be disposed on a substrate, with each probe present in multiple places on the substrate. In another embodiment, one probe may be present in multiple places on the substrate having under different conditions, for example, temperature, pH, chemical environment, and/or any other appropriate conditions or combinations thereof.

Reporter molecule as used herein is not limited to one reporter molecule.

The present invention together with the above and other advantages may best be understood from the following detailed description of the embodiments of the invention illustrated in the drawings.

BRIEF DESCRIPTION OF THE FIGURES

FIGS. 1, 1a, 1b, 1c, 1d, 1e, 2, 2a, 2b, 2c, 3, 3a, 3b, 3c, 4, 5, 6, 6a and 6b illustrate embodiments of molecular detection utilizing a molecular probe, a reporter molecule and an amplification reaction of the present invention.

DETAILED DESCRIPTION OF THE INVENTION

Figure 6:
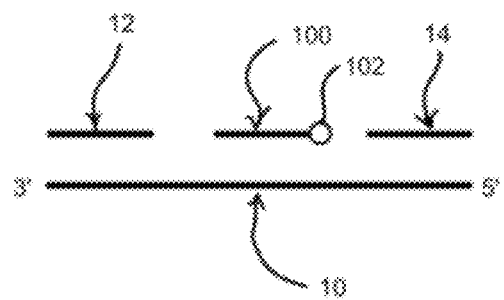

The detailed description set forth below is intended as a description of the presently exemplified device provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

This invention relates to methods for molecular detection, for example to methods utilizing target-specific molecular probes, as noted before, for molecular detection. In general, the target-specific molecular probes, in conjunction with reporter molecules, may be used to detect the presence or absence of a specific target or targets in a given sample. The target-specific molecular probes may bind to target molecules, if present, such as for example, generally in competition and/or with higher affinity than to a reporter molecule. In one embodiment, the methods regulate detection of reporter molecules.

In general, the target-specific molecular probes, in conjunction with reporter molecules, may be used to detect the presence or absence of multiple targets at the same time when the reporter molecules are probes specific, and hence correlated to specific targets. This may, for example, be accomplished with sequence specific probes for detection of amplification products from particular reporter molecules.

In exemplary embodiments, target-specific molecular probes include substantially single-stranded nucleic acids and/or modifications thereof. In general, a molecular probe may bind with relatively high specificity to a given target and an example may be or include an aptamer. An "aptamer" refers to a nucleic acid molecule that is capable of binding to a particular molecule of interest or a target with high affinity and specificity. Aptamers may generally include, but are not limited to, single-stranded nucleic acid, such as, for example, single-stranded DNA (ssDNA), single-stranded RNA (ssRNA), and/or a combination thereof; at least a portion of double-stranded nucleic acid, such as, for example, double-stranded DNA (dsDNA), double-stranded RNA (dsRNA), and/or combinations thereof; modified nucleotides and/or other useful molecules, moieties, and/or other functional chemical components, or combinations thereof; or combinations thereof or similar. Aptamers may also include non-natural nucleotides and nucleotide analogs.

The binding of a target molecule or ligand to an aptamer, which may be DNA or RNA, as noted before, may also change the conformation of the aptamer, for example, in some instances. The method of selection of candidate aptamers may be by, but is not limited to, affinity chromatography and the method of amplification by reverse transcription (RT) or polymerase chain reaction (PCR). Aptamers may also be generated, if desired.

Aptamers generally have specific binding regions which are capable of forming complexes with an intended target molecule in an environment wherein other substances in the same environment are not complexed to the aptamer. The specificity of the binding is defined in terms of the comparative dissociation constants (Kd) of the aptamer for its ligand and/or target molecule as compared to the dissociation constant of the aptamer for other materials in the environment or unrelated molecules in general. Typically, the Kd for the aptamer with respect to its ligand and/or target molecule may be at least about 10-fold less than the Kd for the aptamer with unrelated material or accompanying material in the environment, for example. More for example, the Kd may be at least about 50-fold less, even more for example, at least about 100-fold less, and still even more for example, at least about 200-fold less.

An aptamer may typically be between about 10 and about 300 nucleotides in length. More commonly, an aptamer may be between about 30 and about 100 nucleotides in length.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and may be metabolized in a manner similar to naturally occurring nucleotides. Unless otherwise indicated, a particular nucleic acid sequence also implicitly encompasses conservatively modified variants thereof (e.g., degenerate substitutions) and complementary sequences as well as the sequence explicitly indicated. As an example, degenerate substitutions may be achieved by generating sequences in which one or more positions of the aptamer is substituted with mixed-base and/or deoxyinosine residues. Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used herein interchangeably with oligonucleotide, gene, cDNA, and mRNA encoded by a gene.

In general, modified nucleic acid bases may be utilized and may include, but are not limited to, 2'-Deoxy-P-nucleoside-5'-Triphosphate, 2'-Deoxyinosine-5'-Triphosphate, 2'-Deoxypseudouridine-5'-Triphosphate, 2'-Deoxyuridine-5'-Triphosphate, 2'-Deoxyzebularine-5'-Triphosphate, 2-Amino-2'-deoxyadenosine-5'-Triphosphate, 2-Amino-6-chloropurine-2'-deoxyriboside-5'-Triphosphate, 2-Aminopurine-2'-deoxyribose-5'-Triphosphate, 2-Thio-2'-deoxycytidine-5'-Triphosphate, 2-Thiothymidine-5'-Triphosphate, 2'-Deoxy-L-adenosine-5'-Triphosphate, 2'-Deoxy-L-cytidine-5'-Triphosphate, 2'-Deoxy-L-guanosine-5'-Triphosphate, 2'-Deoxy-L-thymidine-5'-Triphosphate, 4-Thiothymidine-5'-Triphosphate, 5-Aminoallyl-2'-deoxycytidine-5'-

Triphosphate, 5-Aminoallyl-2'-deoxyuridine-5'-Triphosphate, 5-Bromo-2'-deoxycytidine-5'-Triphosphate, 5-Bromo-2'-deoxyuridine-5'-Triphosphate, 5-Fluoro-2'-deoxyuridine-5'-Triphosphate, and/or any other appropriate modified nucleic acid base. It may generally be understood that the nucleoside triphosphates (NTPs) listed above may generally refer to any appropriate phosphate of the modified base, such as additionally, for example, monophosphates (NMPs) or diphosphates (NDPs) of the base.

In exemplary embodiments, molecular probes may be generated as aptamers from large random libraries of, for example, nucleic acids, utilizing an iterative process generally referred to as Systematic Evolution of Ligands by Exponential Enrichment (SELEX) and any appropriate variations and/or modifications thereof. In other exemplary embodiments, molecular probes may be provided or selected from large random libraries of, for example, nucleic acids, already generated.

In general, generated aptamers may also be analyzed, such as by sequencing, sequence clustering, folding, conformation and/or shape determination, motif-identification, and/or by any other appropriate method of analysis or combinations thereof. For example, after multiple rounds of selection in SELEX, particular sequence motifs and/or clusters may emerge as dominant. This may be useful, for example, in determining particular aptamer features that may play a substantial role in the binding activity of the aptamers.

In general, the SELEX method may include contacting a library of, for example, nucleic acids with at least one target, such as, for example, whole cell(s); target molecules, such as isolated and/or partially isolated receptor molecules; and/or any other appropriate target. In general, the members of the library that do not bind with some affinity to the target may be washed or otherwise partitioned from the remainder of the library, which may have a given level of binding affinity to the target. Washing and/or partitioning may in general include any appropriate method and/or mechanism of separating non-binding molecules, such as, for example, agitation, aspiration, flushing, and/or any other appropriate method, mechanism, or combination thereof. Flushing and/or otherwise employing a fluid for washing may generally utilize the same or similar fluid as the fluid utilized as the binding environment. The process may be repeated to partition the strongest binding members of the library to a particular target. Binding may generally refer to forming a molecular complex, chemical bond, physical attachment, adsorption, van der Waals interaction and/or any other general intermolecular association, interaction and/or attachment. Also in general, the separating force of the washing and/or partitioning method or mechanism may generally set at least a partial threshold of binding affinity for nucleic acids that may remain after the washing and/or partitioning step. Amplification, such as by PCR and/or other appropriate nucleic acid amplification methods, of the binding library members may also be utilized to increase the numbers of the binding members of the library for subsequent repetitions and for isolation and/or purification of any final products of the process. Embodiments of the SELEX method may generally be utilized to achieve the generation of molecular probes or functional biomolecules of a given binding affinity and/or range of binding affinity. The various steps of SELEX and related protocols or modifications thereof may be performed in general, utilizing appropriate conditions, such as, for example, an appropriate buffer and/or binding environment, which may be, for example, the same or similar to an environment where generated aptamers may be utilized. For cell receptor molecules, an appropriate physiological buffer and/or environment may generally be utilized for SELEX protocols. Collection of product aptamers may be achieved by, for example, elution of the nucleic acids utilizing an unfavorable environment or buffer for binding to the target, such as, for example, high osmolarity solution, which may in general interfere with binding ability of the nucleic acids. Any other appropriate collection method may also be utilized. Details of a basic SELEX protocol may be found in U.S. Pat. No. 5,270,163, entitled "Methods for identifying nucleic acid ligands," the entire contents of which are hereby incorporated by reference. Other SELEX protocols that may generally be utilized and/or modified for an appropriate usage include those found in U.S. Pat. No. 5,789,157, entitled "Systematic evolution of ligands by exponential enrichment: tissue selex," the entire contents of which are hereby incorporated by reference.

The SELEX technique in general, may begin with a large library of random nucleotides or aptamers. The library may then be contacted with a target and the aptamers bound to the target may be separated and amplified for the next round. The binding conditions for each round may be made more stringent than in the previous round until the only remaining aptamers in the pool are highly specific for and bind with high affinity to the target. While aptamers may be analogous to antibodies in their range of target recognition and variety of applications, they may also possess several key advantages over their protein counterparts. For example, they are generally smaller, easier and/or more economical to produce, are capable of greater specificity and affinity, are highly biocompatible and non-immunogenic, and/or can easily be modified chemically to yield improved properties, for example, any desired properties. After selection, the selected aptamers may also be produced by chemical synthesis, which may aid in eliminating batch-to-batch variation which complicates production of therapeutic proteins.

In some exemplary embodiments, SELEX may be performed to generate aptamers utilizing a whole-cell and/or tissue approach. This may be desirable as whole-cell and/or tissue targets may present appropriate target molecules in a "native" state, such as living target cells with active and/or operative target molecules. In some embodiments, non-whole-cell targets may also be utilized, which may include, but are not limited to, purified molecular samples, anchored target molecules, artificial micelles and/or liposomes presenting target molecules, and/or any other appropriate target.

In one aspect, a method for molecular detection includes utilizing a molecular probe paired to a reporter molecule such that the molecular probe impairs the detection and/or amplification of the reporter molecule in the substantial absence of the target molecule of the molecular probe, as noted above. In general, a target molecule may refer to any appropriate targets, which may include, but are not limited to atomic/ionic targets, molecular targets, biomolecules, proteins, molecular complexes, cells, tissues, viruses, and/or any other appropriate target or combinations thereof.

As noted above, a reporter molecule may generally be a molecule that may be substantially detectable and/or experience a substantial change in detectability under certain conditions of an assay. The detectability of the reporter molecule may be, for example, accomplished by regulating amplification of the reporter molecule in an amplification reaction.

In an example, a reporter molecule may bind and/or hybridize with a molecular probe in competition with a target molecule of the molecular probe. The reporter molecule may then be, for example, a single-stranded nucleic acid which may include a conjugate region and/or sequence at least partially complementary to the molecular probe. In some embodiments, the molecular probe may bind with substantially similar affinity to the reporter molecule and the target molecule. For example, the molecular probe may bind to conjugate region of the reporter molecule, such as, more for example, a nucleic acid region having a complementary sequence. In other embodiments, the molecular probe may bind to the target molecule with higher affinity than to the reporter molecule, such as, for example, in a substantially irreversible manner. In general, the affinity for hybridization of the molecular probe to the reporter molecule may be modulated by, for example, modulating the complementarity of the sequences and/or providing non-complementary end (s) on the molecular probe.

In an exemplary embodiment, an example of which is illustrated in FIG. 1, the molecular probe 100 with some specific binding affinity to a target molecule 90 includes a substantially single-stranded nucleic acid or aptamer with 5' end 106 and 3' end 102 which may include a sequence 104 which is at least partially complementary in sequence to a region 204 of a reporter molecule 200, which may be a substantially single-stranded nucleic acid with 5' end 206 and 3' end 202. The molecular probe 100 may further be substantially non-extendable by nucleic acid polymerases, such as by, for example, inclusion of a non-extendable 3' end 102, such as a sequence span that is not complementary to the reporter molecule 200, and/or a modified base, such as a dideoxy-base lacking a 3' —OH group to form a phosphodiester bond. The molecular probe 100 may also be a circular and/or concatenated aptamer or "captamer" which may be substantially non-extendable by virtue of being circular.

Without the presence of a target molecule 90 in a sample, as illustrated in FIG. 1a, the molecular probe 100 may thus be free to hybridize A with the complementary sequence 204 of the reporter molecule 200. The non-extendable molecular probe 100 may then inhibit amplification by polymerase action. This may also be desirable as the molecular probe 100 may also not be amplified or extended by polymerases, which may thus substantially preserve the amount and/or structure of the molecular probe 100 in the system.

In the presence of target molecule 90 in the sample, as illustrated in FIG. 1b, the molecular probe 100 may then bind to the target molecule 90, as shown, where the binding of the target molecule 90 may be, for example, in competition with the reporter molecule 200. This may generally leave at least a portion of the reporter molecules 200 in a system unhybridized to a molecular probe 100. In one exemplary embodiment, at least one primer 300, with 5' end 306, 3' end 302 and sequence 304 which may be at least partially complementary to a portion of the reporter molecule 200, may then be utilized to hybridize B to the reporter molecule 200, such as, for example, at a primer binding region 208, which may be substantially upstream (in the 3' direction on the reporter molecule 200) of the molecular probe binding region 204. In general, a primer may be a short single-stranded nucleic acid, such as for example about 18-22 bases long, which may be at least partially complementary to a template nucleic acid such that hybridization of the primer to the template may be utilized as a starting point for a polymerase to amplify the template. An amplification reaction may then be utilized, such as polymerase mediated primer extension C of the primer 300.

It may be noted that the extension product may share at least a part of the sequence of the molecular probe 100, but it may be generally linked to the sequence of the primer 300, which may at least partially inhibit the function of the extension product as a molecular probe 100 and thus the original amount of functional molecular probe 100 in the reaction may remain substantially constant. The molecular probe 100 may also be not completely complementary to the reporter molecule 200, such that the extension product may not, for example, share enough sequence with the molecular probe 100 to function as a molecular probe 100.

In general, any appropriate quantitative or semi-quantitative nucleic acid amplification reaction may be utilized for amplification and detection. Such reactions may include, for example, various embodiments of polymerase chain reaction (PCR), more for example, quantitative PCR (QPCR). Such quantitative or semi-quantitative nucleic acid amplification reactions may generally include a reporter for determining the amount of nucleic acid present in a sample. For example, the amplification reaction may then produce multiple copies of nucleic acids complementary to the reporter molecule 200 in some relation to the amount of molecular probes 100 bound to target molecules 90. The amplification may thus produce an increased amount of nucleic acids which may be detectable or aid in detection, such as, for example, by nucleic acid recognizing fluorescent dyes, which may include, but are not limited to, ethidium bromide, SYBR dyes (Invitrogen), Quant-it dyes (Invitrogen), and/or any other appropriate dyes or combinations thereof. In general, where amplification products may be single stranded, it may be desirable to utilize single strand specific and/or single strand fluorescing nucleic acid dyes, such as, for example, SYBR Green II, ssDNA or ssRNA Quant-it dyes (all from Invitrogen), and/or any other appropriate dyes or combinations thereof.

As illustrated in the flow diagram of FIG. 1c, the reporter molecule 200, in the absence of target molecule 90, as in step 18, in this embodiment, may be bound to the probe molecules and may thus experience substantially no amplification 20. In such instances, there may then be no substantial detection, such as substantially no fluorescence or no substantial change in fluorescence at step 24. In the presence of target molecule 90, on the other hand, as in step 19, the reporter molecule 200 may experience amplification as in step 22, since there may be unhybridized reporter molecules left, the amount being dependent both on the total amount of probes used and the amount of target molecules in the sample in this embodiment. The amplified products may then be detected, such as by fluorescence at step 26. The detection of the amplified reporter molecules 200 may then be utilized to correlate the amount of target molecule 90 present in a sample. This may generally be referred to as a "lights-on" assay as the "lights on" of the fluorescent dye may generally indicate the substantial presence of target molecule 90. This may be utilized with both linear and circular reporter molecules 200.

In one exemplary embodiment, it may be desirable for the amount of molecular probe 100 and reporter molecule 200 to be in substantially stoichiometrically equal proportions such that there may be substantially no available reporter molecule 200 for amplification in the absence of target molecule 90.

Also in some exemplary embodiments, it may be desirable to sequester, partition and/or otherwise remove any target molecule 90:molecular probe 100 complexes prior to thermal cycling amplification reactions, such as standard PCR. This may be accomplished, for example, by selective filtration and/or chromatographic methods. This may be desirable to aid in preventing or minimizing degradation of the target molecule 90 and/or the complex during the course of the amplification reaction, which may result in hybridization of newly unbound molecular probes 100 to reporter molecules 200. For example, isothermal, helicase-dependent and/or other amplification reactions that may not utilize large temperature changes, such as low temperature shift amplification, may be utilized.

In further exemplary embodiments, the primer 300 may still hybridize to the reporter molecule 200 while the molecular probe 100 may also be hybridized, as illustrated in FIG. 1e. In general, it may be desirable to utilize a polymerase enzyme which may substantially not perform extension of the primer 300 in this situation. This may be accomplished by, for example, utilizing a polymerase which may be substantially lacking and/or deficient in 5'→3' exonuclease activity such that the polymerase may be substantially unable to remove the hybridized molecular probe 100 to perform primer extension. For example, the so called Stoffel Fragment of the heat-stable polymerase Taq and the Klenow Fragment of DNA polymerase I of *E. Coli* are substantially deficient in 5'→3' exonuclease activity. It may further be desirable to utilize polymerases that may be substantially lacking and/or deficient in strand displacement activity such that the polymerase may substantially not displace any hybridized molecular probe 100 to perform primer extension. Other methods of substantially preventing displacement and/or degradation of the hybridized molecular probe 100 may include, but are not limited to, utilizing a polymerase that may not substantially repair single-stranded breaks while making the gap D between the 3' end of the primer 300 and the 5' end of the molecular probe 100 as small as possible, thus substantially permanently attaching the hybridized molecular probe 100 to the reporter molecule 200 such as by, for example, via cross-linking or photocrosslinking utilizing an appropriate cross-linking agent or photocrosslinking agent and/or crosslinkable nucleotide base and radiation (such as ultraviolet), and/or any other appropriate methods or combinations thereof. Non-specific attachment reactions and/or procedures may also be performed before the addition of primer 300 such that the primer 300 may not substantially become permanently attached to the reporter molecule 200.

In some embodiments, an example of which is illustrated in the flow diagram of FIG. 1d, a sample 80 which may contain target molecule 90 may be first contacted at step 82 with a substantially known amount of molecular probe 100. In general, it may be desirable for the molecular probe 100 to bind to the target molecule 90 in a known proportion, such as, for example, one probe 100 to one target molecule 90. The reporter molecule 200 may then be added in a substantially known amount at step 84 such that any remaining unbound molecular probes 100 may hybridize to the reporter molecules 200, as noted above. At least one primer 300 may then be added to hybridize to the reporter molecules 200 at step 86 and at an amplification/detection step 88, an amplification reaction may then be utilized to amplify the reporter molecules 200 not hybridized to a molecular probe 100, the products of which may then be detected, as above. Selective filtration steps for, as examples, complexes of and/or uncomplexed reporter molecules, target molecules, molecular probes, and/or other components of an assay, may be utilized at any appropriate point during an assay.

In other embodiments, an example of which is illustrated in FIG. 2, a molecular probe 100' may include an extendable single-stranded nucleic acid which may bind with sequence 104, 5' end 106 and an extendable 3' end 102', and may substantially act as a primer for the reporter molecule 200', which may include a region 204 which may be substantially complementary to the molecular probe 100'. In the presence of target molecule 90, such as illustrated in FIG. 2a, the molecular probe 100' may be bound to the target molecule 90 and thus it may not act as a primer for the reporter molecule 200, which may result in substantially no amplification of the reporter molecule 200. Thus, in the absence of target molecule 90, such as illustrated in FIG. 2b, the molecular probe 100' may hybridize to the reporter molecule 200 and act as a primer which may be extended C in an amplification reaction, as noted above. As illustrated in the flow diagram of FIG. 2c, the reporter molecule 200' in the absence of target molecule 90, such as at step 18', may experience amplification 20' and may thus be detected at step 24', such as by fluorescence, as illustrated. If the target molecule 90 is present in a substantial amount, such as at step 19', the reporter molecule 200' may experience substantially no amplification 22' and thus substantially no amplification products may be detected at step 26', such as a substantial lack of fluorescence or "lights off," as illustrated. Thus the detection of amplification product may generally correlate to the absence of target molecule 90 in a sample while the detection of substantially no amplification product (or very little) may generally correlate to the presence of target molecule 90. This form of assay may generally be referred to as "lights-off" as a fluorescent reporter would be "lights off" in the substantial presence of target molecule. This may be utilized with both circular and linear reporter molecules.

In general, the detection limit for the target molecule 90 for a lights-off assay, such as in FIGS. 2, 2a, 2b and 2c, may be directly related to the amount of molecular probes 100' in the system. For example, since the molecular probe 100' serves as a primer, the maximum number of amplification products may be the number of molecular probes 100' in the system since each probe 100' is consumed in the amplification.

In some exemplary embodiments, as illustrated in FIG. 3, a reporter molecule 400 may include a circular single-stranded nucleic acid. As illustrated in FIG. 3a, the reporter molecule 400 may in general hybridize A to a complementary region 404 of the molecular probe 100 in the absence of a target molecule 90, as above. The molecular probe 100 may then inhibit amplification of the reporter molecule 400, such as through non-extendability at the 3' end 102, as noted above. In the embodiments where there is the presence of a target molecule 90, such as illustrated in FIG. 3b, the molecular probe 100 may be bound to the target molecule 90 and then at least one primer 300 may be utilized to hybridize B to a complementary region 408 to amplify the reporter molecule 400 through, for example, primer extension. In some embodiments, it may be desirable, for example, to utilize rolling circle amplification or a similar amplification reaction on a circular reporter molecule 400. In rolling circle amplification, for example, a polymerase may extend the primer hybridized to the circular template, as in standard PCR. The polymerase may then continue extension around the circular template for the duration of the amplification as the circular template may not include any defined end or point of termination of extension. This may be desirable as a relatively large amount of amplification product may be generated without the typical melting and annealing steps of standard PCR. The amplification product may generally be a linear single-stranded nucleic acid which may be a concatenation of the complementary sequence of the circular template.

In some embodiments, the reporter molecule may also be concatenated. For example, the reporter molecule may include multiple copies of binding regions for primers and molecular probes, such as, for example, arranged linearly. In one embodiment, the reporter molecule may be circular and concatenated. This reporter molecule may then be compatible with, for example, rolling circle amplification.

In some aspects, rolling circle amplification may utilize nucleic acid polymerases that may include strand displacement activity. Strand displacement activity may be useful in displacing the amplified product from the template as the polymerase circles around and meets the starting end (e.g. the 5' end of original primer). An example of this is illustrated in FIG. 3c, where the 5' region 152 of the amplification product 150 is displaced as the primer extension C at the 3' end 153 encounters its hybridized portion as it proceeds around the reporter molecule 400. Without the displacement activity, the amplification may not substantially continue as the hybridized strand may block the polymerase from continuing to read the circular template.

In an exemplary embodiment, the primer 300 for a "lights-on" rolling circle amplification, an example of which is illustrated in FIG. 3, 3a, 3b or 3c, may share at least a portion of its sequence with the molecular probe 100. For example, the complementary regions 408, 404 on the reporter molecule 400 for the primer 300 and the molecular probe 100, respectively, may substantially overlap or the primer region 408 may also be part of the molecular probe region 404, as illustrated in FIG. 4. In this manner, the molecular probe 100 may preferentially hybridize to the reporter molecule 400, such as, for example, by virtue of the greater amount of complementary sequence as the molecular probe 100 may generally be longer in sequence than the primer 300. The hybridization affinities of the primer 300 and the molecular probe 100 may also be modified, such as discussed above, to aid in producing a desired preferential hybridization of the molecular probe 100 to the reporter molecule 200. This may be desirable as the molecular probe 100 may substantially exclude the hybridization of the primer 300 and in the case of a non-extendable molecular probe 100, no amplification of the reporter molecule 200 may occur for lack of an extendable primer. This may be useful in utilizing polymerases that may have strand displacement activity such that by, for example, excluding the primer 300 from hybridizing, the polymerase may not substantially displace the hybridized molecular probe 100 by extending a hybridized primer 300. It may further be desirable to utilize polymerases that may be lacking and/or deficient in 5"→3' exonuclease activity, as discussed above. An example of a polymerase may include, but is not limited to, Phi29 polymerase (marketed as RepliPHI by Epicentre Biotechnologies), and/or any other appropriate polymerase.

As discussed above, the molecular probe 100 may also be substantially permanently attached to the reporter molecule 200 such that it may not be readily removable by a polymerase. Other methods of preventing displacement of the hybridized molecular probe 100, such as those discussed above, may also be utilized.

In another embodiment, the primer 300 for a "lights-on" rolling circle amplification may bind directly adjacent to the binding site 404 of the molecular probe 100 on the reporter molecule 400 at region 408, as illustrated in FIGS. 3, 3a and 3b. For example, there may be no sequence gap between the primer 300 and the molecular probe 100 when both are hybridized to the reporter molecule 400, such as with no intervening sequence between regions 404 and 408. The molecular probe 100 and the primer 300 may then be attached and/or connected, such as, for example, by a ligation reaction, such that the 5' end of the molecular probe 100 and the 3' end primer 300 may become joined as a single nucleic acid strand. This may be desirable as the ligation may present no strand breakage or "knick" for a polymerase enzyme to recognize, as a knick may serve as a starting point for polymerase action and polymerases with sufficient strand-displacement activity may displace some of the hybridized molecular probe 100. In this embodiment, a polymerase enzyme may be utilized that may have strand-displacement activity, as the primer 300 and molecular probe 100 may no longer be separate entities where displacement of the molecular probe 100 may impair the functionality of the assay.

In general, nucleic acid ligases may be utilized to ligate the primer 300 to the adjacent hybridized molecular probe 100. Nucleic acid ligases are enzymes that covalently join two nucleic acids by catalyzing the formation of phosphodiester bonds at the ends of the phosphate backbone of the nucleic acids. Examples of appropriate nucleic acid ligases may include, but are not limited to, E. coli DNA ligase, T4 DNA ligase, T4 RNA ligase, strand break DNA repair enzymes, and/or any other appropriate ligase, modified enzyme, and/or a combination thereof. In general the ligase utilized may be selected based on the form of ligation performed, such as ligation of blunt ends, compatible overhang ("sticky") ends, single stranded DNA, singe stranded RNA and/or any other form of ligation. Further in general, the steps in ligating two nucleic acids together is a one step process that may be carried out at or near room temperature. The knick between the primer 300 and the molecular probe 100 may, for example, be "repaired" by a single-strand breakage repairing ligase, such as, for example, T4 DNA ligase. Photo ligation may also be employed. Photo ligation may, for example, include covalently linking adjacent nucleic acids by application of electromagnetic energy, such as ultraviolet or visible light. Coupling agents may also be utilized to facilitate the formation of covalent linkages.

In another embodiment, the reporter molecule 200' of FIGS. 2, 2a, 2b and 2c may be a circular nucleic acid 200" with a molecular probe binding region 204", as illustrated in FIG. 5. This may, for example, perform in a substantially similar way to the reporter 200' of FIGS. 2, 2a, 2b and 2c, but may utilize rolling circle amplification, as discussed above.

In general, for any appropriate embodiment(s), a reverse primer may also be utilized to hybridize to the amplification product for amplification thereof. It may be desirable for the reverse primer to be substantially non-hybridizing with the molecular probe such that the amount of molecular probe remains substantially constant.

Figure 6A:
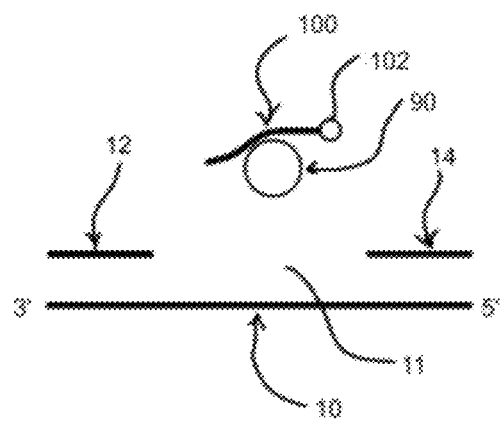
Figure 6B:
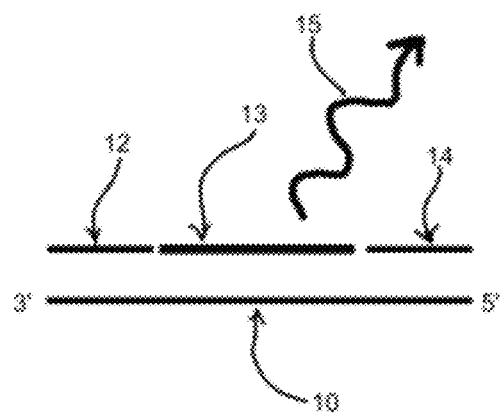

FIG. 6 illustrates a further example of an aptamer-mediated molecular detection method. A nucleic acid strand 10 may contain a conjugate region to an aptamer 100. The aptamer 100 includes a feature 102 which may substantially prevent extension by an amplification reaction, such as PCR. The primers 12 and 14 are also provided for the nucleic acid strand 10. The absence of target molecule 90 may generally result in the aptamer 100 binding to the conjugate region of the nucleic acid strand 10, as shown in FIG. 6. The aptamer 100 thus blocks the amplification of the nucleic acid strand 10 during the primer extension step of the amplification reaction. In the presence of target molecule 90 however, as shown in FIG. 6a, a substantially proportional amount of the aptamer 100 may associate with the target molecule 90 and may thus free a substantially proportional amount of nucleic acid strand 10 for amplification, as illustrated with aptamer 100 binding to target 90 and disassociating from nucleic acid strand 10, leaving the conjugate region 11 open. The amplification, as shown in FIG. 6b, may thus result in a proportional change in the reporter for the reaction which may be quantified and/or analyzed to determine the amount of target molecule present, such as illustrated with the amplification extension 13 occurring between primers 12 and 14, which may produce a reporter signal 15, such as a fluorescence signal. It is noted that the extension 13, while it may share sequence with the aptamer 100, is generally linked to the sequence of at least the primer 12 and/or the primer 14, which may at least partially inhibit the aptamer function such that the original amount of functional aptamer in the reaction remains constant.

In some embodiments, a second primer, such as primer 14 illustrated in FIGS. 6, 6a and 6b, may be utilized, for example, to restrict the length of the amplification product 13. A second primer may also, for example, be utilized to produce a competitive second amplification product.

The present methods may present one or more advantages over other detection methods, such as, for example:
- Production and purification of mono- or polyclonal antibodies is not necessary;
- There is no need to label the target analytes (proteins) in the sample;
- The assay may have no solid phase components;
- Competition in affinity between aptamer:analyte and aptamer:nucleic acid strand may be readily modulated by adjusting complementarity of nucleic acid strand and/or PCR annealing conditions;
- Aptamers may have significantly higher affinity and/or discriminating ability for targets over other molecular probes such as antibodies;
- Nucleic acids are generally less expensive and easier to produce than proteins such as antibodies;
- The linear range of analyte detection may be fine-tuned by simple change of amounts of nucleic acid strand and aptamer as well as ratios thereof;
- Several overlapping ranges may be applied if necessary to give a wide dynamic detection range with little penalty in reagents or setup time; and/or
- The assay may be readily adapted to several established nucleic acid detection, quantitation, and next-generation sequencing technologies for massive multiplexing.

The approach described herein may substantially avoid many problems by developing a sensing chemistry including entirely nucleic acids that are simple enough to be readily multiplexed. For individual analytes, the assay is readily adapted to conventional endpoint PCR as well as quantitative, real-time PCR for highly accurate, rapid results. For the highly multiplexed proteomics application, the chemistry may be coupled with next generation array sequencers (e.g. Illumina, 454, ABI Solid) such that each sequence generated indicates the identification of a particular protein in a sample, and the frequency of the aptamer sequences appearing will indicate relative quantitation. Due to the wide variety of molecular targets which aptamers can recognize, the assay can be expanded to quantify virtually any compound in addition to the protein focus put forth herein.

In addition to the goal of aptamer-mediated sensing with amplification, sequence-specific inhibition of PCR or "SIP", for other purposes related to molecular microbiology may also be desirable. For instance, in bacterial genetics, it may be highly useful in certain contexts to inhibit the amplification of genetic material from a known, high-abundance background or commensal organism.

The following examples illustrate non-limiting embodiments of the invention:

1. Example of Sequence-specific Inhibition of PCR

Figure 7:
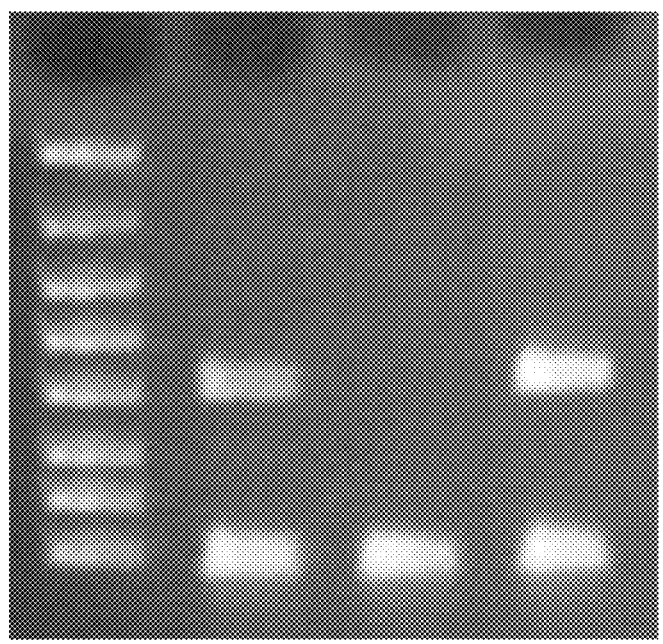
FIG. 7 shows an example of sequence-specific inhibition of an amplification reaction of the present invention.

An *E. coli*-specific, non-extendable blocking oligonucleotide, "EcBlock" to inhibit the amplification of that species was designed. FIG. 7 shows a demonstration of SIP. Three reactions were each set up with a universal "Lane-BC" primer pair. The lanes in the 1% agarose gel were as follows: Lane 1: DNA ladder; Lane 2: Standard PCR with *E. coli* genomic DNA template; Lane 3: PCR reaction with *E. coli* template and Ecblock; Lane 4: PCR reaction with *B. cepacia* genomic DNA template and Ecblock. Sequence-specific inhibition of PCR was accomplished by incorporating 4-6 bases at the 3'-end of the blocker which were non-complementary to the template DNA.

In addition to the example above, a number of other options for blocking extension are possible including dideoxy bases, fluorescent nucleotides or other chemically modified "bulky" groups, and/or any other appropriate extension blockers.

2. Example of PCR of a Template Complementary to an Aptamer

In this example, a 213 bp DNA template was ordered from a gene synthesis company (Epoch Biolabs, Stafford, Tex). The DNA template was designed to comprise regions for priming and an interprimer region complementary to a known aptamer to a clinically important protein, vascular endothelial growth factor (VEGF). A preliminary system for detection (and quantifying) VEGF using the DNA aptamer to VEGF, 5'-CCG TCT TCC AGA CAA GAG TGC AGG G-3' (SEQ ID NO 1) was designed. The template DNA sequence was 5'-P120 . . . Rnd170 . . . ATGCCCCTG-CACTCTTGTCTGGAAGACGG . . . Rnd270 . . . P220-3' (SEQ ID NO 2), wherein P120 and P220 represent regions of 20 bases targeted by primers for PCR. Rnd170 and Rnd270 represent a randomized region of 70 bases.

It will be appreciated by those of ordinary skill in the art that the present invention can be embodied in other specific forms without departing from the spirit or essential character hereof. The present description is therefore considered in all respects to be illustrative and not restrictive. The scope of the present invention is indicated by the appended claims, and all changes that come within the meaning and range of equivalents thereof are intended to be embraced therein.

The invention claimed is:

1. A method for molecular detection comprising:
adding at least one molecular probe to a sample for detecting the presence of a protein target in said sample, said at least one molecular probe comprising an artificial nucleic acid aptamer having a binding affinity for the target;
adding at least one reporter molecule to said sample, said at least one reporter molecule comprising an artificial nucleic acid comprising a circular nucleic acid with a conjugate region designed to be at least partially complementary to said artificial nucleic acid aptamer;
adding at least one primer to said sample, said at least one primer being a separate molecule from said at least one molecular probe; and
performing a quantitative or semi-quantitative amplification reaction on the at least one reporter molecule by primer extension of said primer;
wherein said at least one molecular probe binds to said conjugate region of said at least one reporter molecule in the absence of the target and the binding impairs amplification of said at least one reporter molecule by said at least one molecular probe attaching to said at least one primer by a ligation reaction.

2. The method of claim 1, wherein said at least one molecular probe is added prior to the addition of either of said at least one reporter, primer or both.

3. The method of claim 2, wherein said at least one molecular probe, at least one reporter and at least one primer are added simultaneously.

4. The method of claim 1, wherein said attaching of said at least one molecular probe to said at least one primer comprises covalent linkage.

5. The method of claim 1, wherein said reporter molecule is a single-stranded circular nucleic acid.

6. The method of claim 1, wherein said amplification reaction comprises rolling circle amplification.

7. The method of claim 6, further comprising performing said rolling circle amplification utilizing at least one primer substantially complementary to at least a portion of said reporter and at least a portion of its sequence is in common with said molecular probe.

8. The method of claim 7, wherein said rolling circle amplification is performed with a polymerase enzyme having strand displacement activity.

9. A method for molecular detection comprising:
adding at least one molecular probe to a sample for detecting the presence of a protein target in the sample, said at least one molecular probe comprising an artificial nucleic acid and having a binding affinity for said protein target and comprising an artificially modified 3'-residue which is non-extensible by a nucleic acid amplification reaction;
adding at least one reporter molecule to said sample, said at least one reporter molecule comprising a nucleic acid having a first region substantially complementary to said at least one molecular probe and a second region adjacent to said first region;
adding at least one primer to said sample, said at least one primer comprising a nucleic acid and being substantially complementary to said second region and being a separate molecule from said at least one molecular probe;
performing a ligation reaction on said molecular probe and said primer which are bound to said first and second regions, respectively, of said reporter molecule to form an extended primer which is non-extensible by a nucleic acid amplification reaction; and
performing a quantitative or semi-quantitative nucleic acid amplification reaction on said at least one reporter molecule by primer extension of said at least one primer bound to said second region;
wherein said at least one molecular probe binds competitively to said protein target and said first region, said primer extension of said at least one primer being inhibited by formation of said extended primer.

10. The method of claim 9, wherein said first region is upstream (5') of said second region.

11. The method of claim 9, further comprising sequestering any protein target:molecular probe complexes prior to performing said ligation reaction.

12. The method of claim 9, wherein said reporter molecule is a circular nucleic acid.

13. The method of claim 12, wherein said amplification reaction comprises rolling circle amplification.

14. The method of claim 9, wherein said ligation reaction comprises adding a ligase to said sample.

15. The method of claim 14, wherein said ligase is selected from the group comprising *E. coli* DNA ligase, T4 DNA ligase, T4 RNA ligase, and a strand break DNA repair enzyme.

16. The method of claim 9, wherein said ligation reaction comprises photo-ligation.

17. The method of claim 1, wherein said primer extension of said primer generates an amplification product in an amount proportional to the amount of said protein target present in said sample.

18. The method of claim 9, wherein said primer extension of said primer generates an amplification product in an amount proportional to the amount of said protein target present in said sample.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:

-continued

```
<223> OTHER INFORMATION: artificial DNA sequence, completely synthesized
      DNA aptamer to human (Homo sapiens) VEGF

<400> SEQUENCE: 1
ccgtcttcca gacaagagtg caggg                                            25

<210> SEQ ID NO 2
<211> LENGTH: 29
<212> TYPE: DNA
<213> ORGANISM: Artificial Sequence
<220> FEATURE:
<223> OTHER INFORMATION: artificial DNA sequence, completely synthesized
      DNA containing complementary region to SEQ ID NO 1

<400> SEQUENCE: 2
atgcccctgc actcttgtct ggaagacgg                                        29
```